United States Patent [19]

Belliotti et al.

[11] Patent Number: 5,348,957

[45] Date of Patent: * Sep. 20, 1994

[54] 5-HYDROXY-2-PYRIMIDINYLMETHYLENE DERIVATIVES USEFUL AS ANTIINFLAMMATORY AGENTS

[75] Inventors: Thomas R. Belliotti, Ypsilanti; David T. Connor, Ann Arbor; Catherine R. Kostlan, Saline, all of Mich.

[73] Assignee: Warner-Lambert Company, Morris Plains, N.J.

[*] Notice: The portion of the term of this patent subsequent to Feb. 11, 2010 has been disclaimed.

[21] Appl. No.: 103,462

[22] Filed: Aug. 6, 1993

Related U.S. Application Data

[60] Division of Ser. No. 909,850, Jul. 7, 1992, Pat. No. 5,270,319, which is a continuation-in-part of Ser. No. 756,400, Sep. 9, 1991, abandoned.

[51] Int. Cl.$^5$ ............... A61K 31/535; A61K 31/495; A61K 31/505
[52] U.S. Cl. ................. 514/235.8; 514/255; 514/269
[58] Field of Search ....... 514/269, 235.8, 255

[56] References Cited

U.S. PATENT DOCUMENTS

| | | | |
|---|---|---|---|
| 4,711,888 | 12/1987 | Walker et al. | 514/269 |
| 4,859,679 | 8/1989 | Santini | 514/273 |
| 4,940,712 | 7/1990 | Walker et al. | 514/272 |
| 5,143,928 | 9/1992 | Cetenko et al. | 514/369 |
| 5,208,250 | 5/1993 | Cetenko et al. | 514/369 |
| 5,270,319 | 12/1993 | Belliotti et al. | 514/269 |

FOREIGN PATENT DOCUMENTS

| | | |
|---|---|---|
| 881752 | 3/1979 | Belgium . |
| 0164204 | 12/1985 | European Pat. Off. . |
| 0233461 | 1/1986 | European Pat. Off. . |
| 0210044 | 1/1987 | European Pat. Off. . |
| 0319170 | 11/1988 | European Pat. Off. . |
| 0373827 | 6/1990 | European Pat. Off. . |
| 1476534 | 5/1965 | France . |
| 1216978 | 2/1988 | Japan . |

OTHER PUBLICATIONS

*J. Med. Chem.*, 1990, 33, pp. 1892–1898; Lazer et al.
*J.C.S. Perkin I*, 1976, pp. 1202–1204; Roeterdink, et al.
*Chem. Ber.*, 1960, pp. 1998–2001; Dornow, et al.
*Indian Journal of Chemistry*, vol. 24B, 1985, pp. 535–538; Sen, et al.
CA89(15):129478d (1989), Chemical Abstracts.
CA89(13):109333z (1989), Chemical Abstracts.
*Chemical Reviews*, 1975, vol. 75, No. 4, p. 207 and p. 412
*Biochem.*, 1951, vol. 48, pp. 400–407; Bray, et al.

*Primary Examiner*—Raymond J. Henley, III
*Attorney, Agent, or Firm*—Ronald A. Daignault; Charles W. Ashbrook

[57] ABSTRACT

The present invention compounds are 5-hydroxy-2-pyrimidinylmethylene derivatives and pharmaceutically acceptable addition salts, bases, and base salts thereof, pharmaceutical compositions and methods of use therefor. The invention compounds are found to have activity as inhibitors of 5-lipoxygenase and/or cyclooxygenase providing treatment of, for example, inflammation and GI ulcers.

2 Claims, No Drawings

5-HYDROXY-2-PYRIMIDINYLMETHYLENE DERIVATIVES USEFUL AS ANTIINFLAMMATORY AGENTS

CROSS REFERENCE TO RELATED APPLICATION

This is a divisional of U.S. application Ser. No. 07/909,850 filed Jul. 7, 1992, now U.S. Pat. No. 5,270,319 which is a continuation-in-part of U.S. application Ser. No. 02/756,400 filed Sep. 9, 1991, now abandoned.

BACKGROUND OF THE INVENTION

The present invention is novel compounds which are a 5-hydroxy-2-pyrimidinylmethylene derivative and pharmaceutically acceptable acid addition or base salt thereof, pharmaceutical composition and method of use therefor. The invention compounds are found to have activity as inhibitors of one or both 5-lipoxygenase and cyclooxygenase providing treatment of conditions advantageously affected by such inhibition including inflammation, arthritis, pain, fever, and particularly rheumatoid arthritis, osteoarthritis, other inflammatory conditions, psoriasis, allergic diseases, asthma, inflammatory bowel disease, GI ulcers, cardiovascular conditions, including ischemic heart disease and atherosclerosis, and ischemia-induced cell damage, particularly brain damage caused by stroke. They can also be used topically for treating acne, sunburn, psoriasis, and eczema. Also included are leukotriene-mediated pulmonary, gastrointestinal, inflammatory, dermatological, and cardiovascular conditions. The disclosed compounds also have utility as antioxidants. The preferred method of use for the present invention is in treating inflammatory conditions. Thus, the present invention is also a pharmaceutical composition or method of manufacturing a pharmaceutical composition for the use of treating the noted conditions. 3,5-Ditertiarybutyl-4-hydroxyphenylmethylidene derivatives of thiazolidinones, oxazolidinones, and imidazolidinones are known to provide activity as inhibitors of 5-lipoxygenase and-/or cyclooxygenase. See U.S. application Ser. No. 07/702,132, filed May 13, 1991, now pending; U.S. application Ser. No. 07/640,711, filed Jan. 18, 1991, now pending; and U.S. application Ser. No. 07/426,814, filed Oct. 30, 1989, now pending which is a continuation in part of U.S. application Ser. No. 07/277,171, filed Nov. 29, 1988, now abandoned. U.S. Ser. No. 07/426,814, U.S. Ser. No. 07/702,132, and U.S. Ser. No. 07/640,711 disclose numerous references having 3,5-ditertiarybutyl-4-hydroxy-benzylidenes and are incorporated by reference therefor. Pyrimidine is not noted in these references. Structure activity relationships of certain ditertiarybutylphenols and homologs thereof are discussed by Lazer, E. S., et al in "Effect of Structure on Potency and Selectivity in 2,6-Disubstituted 4-(2-Arylethenyl)phenol Lipoxygenase Inhibitors of J. Med. Chem. 1990, 33, 1892–1998. Again, pyrimidines are not noted in this reference and so compounds therein differ from the present invention.

An orotic aldehyde condensed with 3-(R-substituted)rhodanines is disclosed in CA89(15):129478d and CA89(13)1093332 useful for complexing selected metal ions. The disclosed formula includes

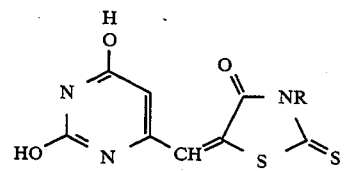

and

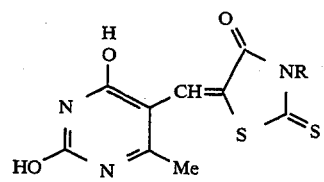

These differ from the present invention by the position of substituents and number of hydroxys on the pyrimidine ring.

Numerous references disclose 2-amino-5-hydroxy pyrimidines. Compounds having other N containing groups in place of the amino group are also disclosed, however in each such compound all attachments are at the N of the pyrimidinyl moiety. Such disclosed pyrimidines may also be substituted at the 4- and/or 6-positions with various groups including alkyls. No reference shows 5-hydroxy together with the methylene heterocyclic group in the 2-position as now found in the present invention. For example, UK patent application number 2045736 and the Bioch. J. 1951, 48, p. 400 shown the simple 2-amino-5-hydroxy-4,6-dimethylpyrimidine. Other substituted 2-aminopyrimidines are shown in European patent application numbers 89312736.5 and 86305466.4 (equivalent to U.S. Pat. No. 4,711,888), European publication numbers 319170, 233416, 164204, and U.S. Pat. Nos. 4,859,679 and 4,940,712.

Japanese Application No. 1,216,978 discloses 2-arylpyrimidines but differs from the present invention, that requires the 5-hydroxy substituent and methyleneheterocyclic substituent.

Pyrimidinylmethylene compounds have been described in CA 89(15)1294786 and CA 89(13)1093332 but differ in position of substituents and number of hydroxys.

5-OH pyrimidines have been described but none has the methylene heterocycle substituent at the 2-position.

Further, although French Application No. 1,476,534 presents a generic scope including various 2-substituted pyrimidines this French application differs from the present invention by failing to provide the present invention substituent combinations.

The disclosures in Chem. Ber. (1960), p. 1998–2001 and in The Indian Journal of Chemistry, Vol. 24B, May 1985, pp. 535–538, showing oxazole to pyrimidine ring transformations and the disclosure in Chemical Reviews 1975, Vol. 75, No. 4, pp. 207 and 412 showing a preparation of an oxazole and subsequent transformation to pyrimidine all show a synthesis and product having substituents in the 4- and 6-positions. These differ from the present invention by the failure to show a methylidene bridge between the heterocyclic ring.

In summary, the references of record show neither the present 2-substituent nor combinations of 4- and 6-substituents with a 5-hydroxy group and combinations of these with a methyleneheterocyclic group.

Thus, the references noted above differ from the present 5-hydroxy-2-pyrimidinylmethylidene or 4,6-dilower alkyl-5-hydroxy-2-pyrimidinyl methyleneheterocycles.

SUMMARY OF THE INVENTION

Copending U.S. applications Ser. No. 07/648,115, filed Jan. 31, 1991 provides unsubstituted aryl and heteroaryl analogs of 4,6-ditertiarybutyl-5-hydroxy-2-pyrimidines which inhibit one or both of 5-lipoxygenase and cyclooxygenase for use in the above noted conditions.

Copending U.S. application Ser. No. 07/648,114, filed Jan. 31, 1991 provides substituted heteroaryl analogs of 4,6-ditertiarybutyl-5-hydroxy-2-pyrimidines which inhibit one or both of 5-lipoxygenase and cyclooxygenase for use in treatment of the above noted diseases or conditions. Although both these applications include both a direct and an ethenylenyl linkage the present invention differs by both the methylidene linking group and the ring system linked to the pyrimidinyl group thereby. Regarding the present ring system, differences include at least one carbonyl in the ring.

The present invention is a compound of the formula (I)

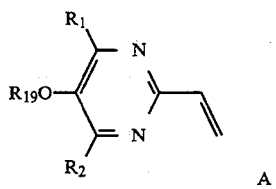

or a pharmaceutically acid addition or base salt thereof; wherein
$R_1$ and $R_2$ are independently hydrogen and lower alkyl;
$R_{19}$ is H or acetyl;
A is
1)

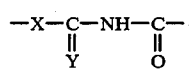

wherein
X is S, O, NH, or $CH_2$; and
Y is S, O, or NH;
2)

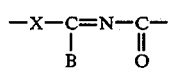

wherein
X is as defined above; and
B is
i) $SR_7$,
ii) $SOR_7$,
iii) $SO_2R_7$,
iv) $NR_{15}R_{16}$,
v) NHCN,
vi)

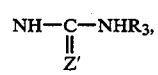

vii)

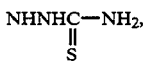

viii)

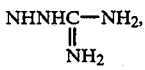

ix) $N(OR_6) R_4$,
x) $N(OH)COR_5$,
xi) $NR_4W$,
xii) $S(CH_2)_nCO_2R_6$, or
xiii) $NR_7COR_6$
wherein
Z' is S, O, NH, or NCN;
W is $CO_2R_7$,

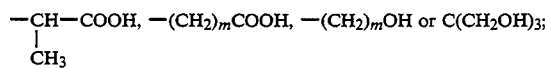

n is 1, 2, or 3;
m is 1, 2, 3, 4, or 5;
$R_{15}$ and $R_{16}$ are independently H, lower alkyl, aralkyl, or $(CH_2)_nNR_6R_7$
wherein n is as defined above;
$R_3$ is H, alkyl, or aryl;
$R_4$ is H or alkyl;
$R_5$ is alkyl, aryl, or $CF_3$;
$R_6$ is H or lower alkyl; and
$R_7$ is lower alkyl;

3)

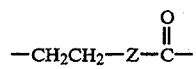

wherein Z is $CH_2$, S, O, or $NR_8$ wherein $R_8$ is H, lower alkyl, OH, or OMe;

4)

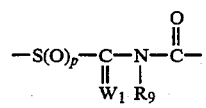

wherein
p is 0, 1, or 2;
$W_1$ is $H_2$, O, or S;
$R_9$ is
i) lower alkyl,
ii) lower alkenyl,
iii) $SO_2CH_3$,
iv) $OR_{10}$,
v)

vi) $NR_{12}R_{13}$, or
vii) $-(CH_2)_nY_1$
wherein a) n is as defined above;
b) R$_{10}$ is H, lower alkyl, tosyl, or

c) Y$_1$ is —CN, —OR$_{10}$, SH, SR$_7$,

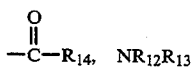

wherein R$_{12}$ and R$_{13}$ are as defined herein,
wherein,
R$_7$ and R$_{10}$ are as defined above;
R$_{11}$ is lower alkyl, lower alkoxy, or NH$_2$
R$_{14}$ is —OH, lower alkyl, lower alkoxy, or NH$_2$
R$_{12}$ and R$_{13}$ are each independently H, lower alkyl, lower alkenyl, (CH$_2$)qOH, (CH$_2$)qNR$_{17}$R$_{18}$, or (CH$_2$)qSR$_7$, or R$_{12}$ and R$_{13}$ taken together form a morpholinyl, piperidinyl, piperazinyl, or an N-methyl piperazinyl ring;
wherein
R$_7$ is as defined above;
q is an integer of 1-6;
R$_{17}$ and R$_{18}$ are independently lower alkyl.

The present invention is also a pharmaceutical composition for the treatment of conditions advantageously affected by the inhibition of one or both of 5-lipoxygenase and cyclooxygenase which comprises an amount effective for the treatment of the condition of a compound of the formula I and the pharmaceutically acceptable acid addition or base salt thereof together with a pharmaceutically acceptable carrier. The condition is meant to include, for example, a condition as listed above which is advantageously affected by such inhibition of one or both of 5-lipoxygenase and cyclooxygenase, preferably, arthritis or other inflammatory diseases, allergic diseases, pain, fever, and psoriasis, but more preferably inflammatory conditions or diseases.

The present invention is also a method for treatment of the condition as noted above in a mammal, including humans, suffering therefrom with a compound of the formula I or the pharmaceutically acceptable acid addition or base salt thereof, in unit dosage form. The invention also provides for use of any such compound of formula I or salt thereof in the manufacture of medical therapeutic agent.

Pharmaceutical composition or use of the compound or salt of formula I is meant to include treatment understood to be prophylactic pertinent to the foregoing named condition.

Preferred compounds of the present invention are compounds of the formula I wherein R$_1$ and R$_2$ are tertiarybutyl.

DETAILED DESCRIPTION OF THE INVENTION

In the compounds of formula (I) the term "lower alkyl" includes an alkyl group of from one to six carbons such as methyl, ethyl, propyl, butyl, and the like and isomers thereof.

Halogen is chloro, bromo or fluoro.
Aryl is phenyl unsubstituted or substituted by one, two, or three substituents of one or more of each of alkyl of one to four carbons, inclusive, OR$_4$ wherein R$_4$ is independently as defined above, SR$_4$ wherein R$_4$ is independently as defined above,

wherein R$_4$ is independently as defined above, C(O)R$_4$ wherein R$_4$ is independently as defined above, hydroxymethyl, NR$_4$R$_6$ wherein R$_4$ and R$_6$ are each independently as defined above, or nitro, CF$_3$, or halogen as defined above.

Aralkyl is an aryl as defined above and attached through an alkylenyl such as methylenyl, ethylenyl, propylenyl, butylenyl, and isomers thereof.

Me is methyl.

The compounds of the invention may contain geometric isomers. Thus, the invention includes the individual isomers and mixtures thereof. The individual isomers may be prepared or isolated by methods known in the art.

A tautomeric form of selected compounds of formula I would be recognized by an ordinarily skilled artisan to be within the present invention.

Appropriate compounds of formula I are useful in the free base form, in the form of base salts where possible, and in the form of acid addition salts. The three forms are within the scope of the invention. In practice, use of the salt form amounts to use of the base form. Pharmaceutically acceptable salts within the scope of the invention may be those derived from mineral acids such as hydrochloric acid and sulfuric acid; and organic acids such as methanesulfonic acid, ethanesulfonic acid, benzenesulfonic acid, p-toluenesulfonic acid, and the like, giving the hydrochloride, sulfonate, methanesulfonate, ethanesulfonate, benzenesulfonate, p-toluenesulfonate and the like, respectively, or those derived from bases such as suitable organic and inorganic bases. Examples of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines such as methylamine, dimethylamine, and triethylamine; mono-, di-, or trihydroxyalkylamines such as mono-, di-, or triethanolamine; amino acids such as arginine and lysine; guanidine; choline N-methylglucosamine; N-methylglucamine; L-glutamine; N-methylpiperazine; morpholine; ethylenediamine; N-benzylphenethylamine; tris(hydroxymethyl)aminomethane; and the like. (See for example, "Pharmaceutical Salts," *J. Pharm. Sci.,* 66(1):1-19 (1977).) Salts of inorganic bases include sodium, potassium, calcium or the like.

The acid addition salts of said basic compounds are prepared either by dissolving the free base or acid of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution. Salts can also be prepared by adding base to an aqueous alcohol solution of another salt.

The compounds of the invention may contain geometric or optical isomers. Thus, the invention includes the individual isomers and mixtures thereof. The individual isomers may be prepared or isolated by methods known in the art.

The compounds of the invention may contain an asymmetric carbon atom, particularly, for example, in the side chain of the compounds of formula I. Thus, the invention includes individual enantiomers, the pure S, the pure R isomer, and mixtures thereof. The individual enantiomers may be prepared or isolated by methods known in the art. Likewise diastereomers are included in the invention if possible, both as individuals or mixtures thereof.

Hydrates of compounds of formula I, if possible, are also the present invention and are prepared or isolated by conventional methods known to an ordinarily skilled artisan.

In determining when a lipoxygenase, cyclooxygenase, or dual lipoxygenase/cyclooxygenase inhibitor is indicated, of course inter alia, the particular condition in question and its severity, as well as the age, sex, weight, and the like of the subject to be treated, must be taken into consideration and this determination is within the skill of the attendant physician.

For medical use, the amount required of a compound of formula (I) or pharmacologically acceptable salt thereof to achieve a therapeutic effect will, of course, vary both with the particular compound, the route of administration, the mammal under treatment, and the particular disorder or disease concerned. A suitable dose of a compound of formula (I) or pharmacologically acceptable salt thereof for a mammal suffereing from, or likely to suffer from any condition as described hereinbefore is 0.1 $\mu$g–500 mg of the compound per kilogram body weight. In the case of systemic administration, the dose may be in the range of 0.5 to 500 mg of the compound per kilogram body weight, the most preferred dosage being 0.5 to 50 mg/kg of mammal body weight administered two or three times daily. In the case of topical administration, e.g., to the skin or eye, a suitable dose may be in the range 0.1 ng-100 $\mu$g of the compound per kilogram, typically about 0.1 $\mu$g/kg.

In the case of oral dosing for the treatment or prophylaxis of arthritis or inflammation in general, due to any course, a suitable dose of a compound of formula I or physiologically acceptable salt thereof, may be as specified in the preceding paragraph, but most preferably is from 1 mg to 10 mg of the compound per kilogram, the most preferred dosage being from 1 mg to 5 mg/kg of mammal body weight, for example from 1 to 2 mg/kg.

It is understood that the ordinarily skilled physician or veterinarian will readily determine and prescribe the effective amount of the compound to prevent or arrest the progress of the condition for which treatment is administered. In so proceeding, the physician or veterinarian could employ relatively low doses at first, subsequently increasing the dose until a maximum response is obtained.

While it is possible for an active ingredient to be administered alone, it is preferable to present it as a pharmaceutical formulation comprising a compound of formula I or a pharmacologically acceptable acid addition or base salt thereof and a pharmacologically acceptable carrier therefor. Such formulations constitute a further feature of the present invention.

The formulations, both for veterinary and for human medical use, of the present invention comprise an active ingredient in association with a pharmaceutically acceptable carrier thereof and optionally other therapeutic ingredient(s). The carrier(s) must be 'acceptable' in the sense of being compatible with the other ingredients of the formulations and not deleterious to the recipient thereof.

The formulations include those in a form suitable for oral, pulmonary, ophthalmic, rectal, parenteral (including subcutaneous, intramuscular, and intravenous), intraarticular, topical, nasal, or buccal administration. Such formulations are understood to include long-acting formulations known in the art.

The formulations may conveniently be presented in unit dosage form and may be prepared by any of the methods well-known in the art of pharmacy. All methods may include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units such as capsules, cachets, tablets, or lozenges, each containing a predetermined amount of the active ingredient; in the form of a powder or granules; in the form of a solution or a suspension in an aqueous liquid or nonaqueous liquid; or in the form of an oil-in-water emulsion or a water-in-oil emulsion. The active ingredient may also be in the form of a bolus, electuary, or paste.

The usefulness of the compounds of the present invention as inhibitors of the 5-lipoxygenase enzyme, cyclooxygenase, or in treating related diseases or conditions may be demonstrated by their effectiveness in various standard test procedures. A description of each procedure follows.

ARBL/ARBC WHOLE CELL 5-LIPOXYGENASE AND CYCLOOXYGENASE ASSAYS

Materials

The rat basophilic leukemia cell line (RBL-1) was obtained from the American Type Culture Collection (Rockville, Md).

Radioimmuoassay (RIA) kits of $LTB_4$ and $PGF_{2\alpha}$ were obtained from Amersham (Arlington Heights, Ill.) and Seragen (Boston, Mass.), respectively.

All tissue culture media were obtained from GIBCO (Grand Island, N.Y.).

Method

RBL-1 cells are grown in suspension culture in Eagle's minimum essential medium supplemented with 12% fetal bovine serum at 37° C. in an incubator supplied with air-5% carbon dioxide. Cells are harvested by centrifugation. They are washed with cold phosphate buffered saline pH 7.4 (PBS; NaCl, 7.1 g; NaHPO, 1.15 g; KHPO, 0.2 g; and KCl, 0.2 g/l). Cells are finally suspended in PBS containing 1.0 mM calcium at a density of 2×10 cells/ml. Cells are incubated with and without test agent (in DMSO) (1% DMSO is without effect on arachidonic acid metabolism) for ten minutes at room temperature. Calcium ionophore A23187 (5 μM) is added and cells are incubated for seven minutes at 37° C. The reaction is stopped by chilling the tubes on ice for ten minutes. Cells are separated by centrifugation and the supernatant is stored at −20°. Aliquots (100 μL) are analyzed for $LTB_4$ and $PGF_{2\alpha}$ using radioimmunoassay kits as provided by the supplier.

Biochemical data obtained from this whole cell assay may be shown as $IC_{50}$s which are calculated as the amount of test compound causing 50% inhibition of $LTB_4$ or $PGF_{2\alpha}$ formation. The following Table exemplifies the data for the present invention.

| Compound of | BIOLOGICAL RESULTS | |
|---|---|---|
| | % Inhibition at 10 μM Conc | |
| Example Number | ARBL | ARBC |
| 6 | 91 | 81 |
| 7 | 32 | 56 |
| 8 | 60 | 68 |
| 15 | 46 | 88 |
| 16 | 100 | 93 |

In addition to the compounds of formula I, the pharmaceutical compositions can also contain other active ingredients, such as cyclooxygenase inhibitors, nonsteroidal antiinflammatory drugs (NSAIDs), peripheral analgesic agents such as zomepirac, diflunisal, and the like. The weight ration of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the formula I and other active ingredients will generally also be within the aforementioned range, but in each case, an effective dose of each active ingredient should be used.

Combinations of a compound of the formula I and other active ingredients will generally be in the aforementioned ratios.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, pirprofen, carprofen, oxaprozin, pranoprofen, microprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefanamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

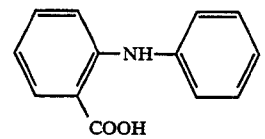

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

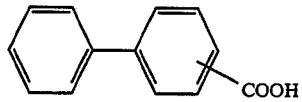

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam, and 4-hydroxyl-1,2-benzothiazine 1,1-dioxide 4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

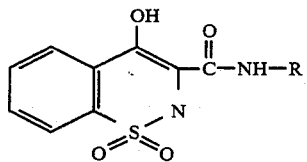

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDs which may also be used include the salicylates, specifically aspirin, and the phenylbutazones, and pharmaceutically acceptable salts thereof.

Pharmaceutical compositions comprising the formula I compounds may also contain as the second active ingredient, antihistaminic agents such as benadryl, dramamine, histadyl, phenergan, and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the formula I may also be advantageously combined with an $H_1$ or $H_2$-receptor antagonist, such as for instance cimetidine, ranitidine, terfenadine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508, and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

The compounds of the formula I and their salts are prepared generally by the following processes and constitute a further aspect of the present invention.

In the following processes Ar=

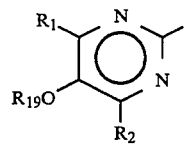

Under certain circumstances as discussed below, it is necessary to protect the phenolic OH of Ar in various intermediates to give QAr where QAr is

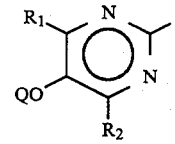

where Q is a suitable oxygen protecting group, preferably methoxyethoxymethyl (MEM).

The MEM group is removed later using 1) Lewis acids such as $ZnBr_2$ in halogenated solvents such as methylene chloride, chloroform, and dichloroethane at 0° to 60° C., 2) mineral acids such as HCl, HBr, or $HNO_3$ in solvents such as water, alkanols, tetrahydrofuran, dialkylethers, dioxane, glyme, diglyme at 0° to 60° C. or 3) organic acids such as acetic acid in the solvents described in 1) and 2) at 0° to 60° C.

Introduction and removal of such suitable oxygen protecting groups are well-known in the art of organic chemistry; see for example "Protective Groups in Organic Chemistry, "J. F. W. McOmie, ed., (New York, 1973), pages 43ff, 95ff, J. F. W. McOmie, *Advances in Organic Chemistry*, Vol. 3, 159-190 (1963); J. F. W. McOmie, *Chem. & Ind.*, 603 (1979), and T. W. Greene, "Protective Groups in Organic Synthesis", Wiley (New York) 1981, Chapters 2, 3, and 7.

Examples of suitable oxygen protecting groups are benzyl, trialkylsilyl, ethoxyethyl, methoxyethoxymethyl, methoxymethyl, trialkylsilylethyl, and the like.

In the process described herein for the preparation of compounds of this invention the requirements for protective groups are generally well recognized by one skilled in the art of organic chemistry, and accordingly the use of appropriate protecting groups is necessarily implied by the processes of the charts herein, although such groups may not be expressly illustrated.

The starting materials for the present invention are prepared as set out below, and as repeated here from copending applications PD-4175-01-JT and PD-4176-01-JT which are incorporated by reference, therefor.

Compound of the formula 3' in Scheme 1' below is prepared from the known haloketone 2' (C. W. Shoppee and D. Stevenson, *J. Chem. Soc. Perkin I*, p. 3015, 1972) by reaction with a salt of acetic acid such as sodium or potassium acetate in a solvent such as DMSO at a reaction temperature of 18° C. to 60° C., or in a solvent such as acetic acid at reflux. Acetoxydiketone 3' is converted to oxazole 4' by treatment with an ammonium salt such as ammonium chloride or preferably ammonium acetate in a solvent such as acetic acid at reflux for 1 to 16 hours or in a solvent such as formamide at 100° to 200° C. for 1 to 6 hours. Alternatively 2' is converted directly to 4' by treatment with acetamide or ammonium acetate in a solvent such as acetic acid at reflux. The oxazole 4' is converted to pyrimidine 5' by treatment with ammonia or an ammonium salt at elevated temperature. Preferably 4' is reacted with concentrated ammonium hydroxide at 150° to 190° C. in a pressure reaction vessel for 6 to 72 hours. 5' is also prepared by reaction of 3' with an ammonium salt such as $NH_4Cl$ or $NH_4OAc$ in a solvent such as formamide at a temperature of 180° to 200° C. for longer periods of time such as overnight to 1 week.

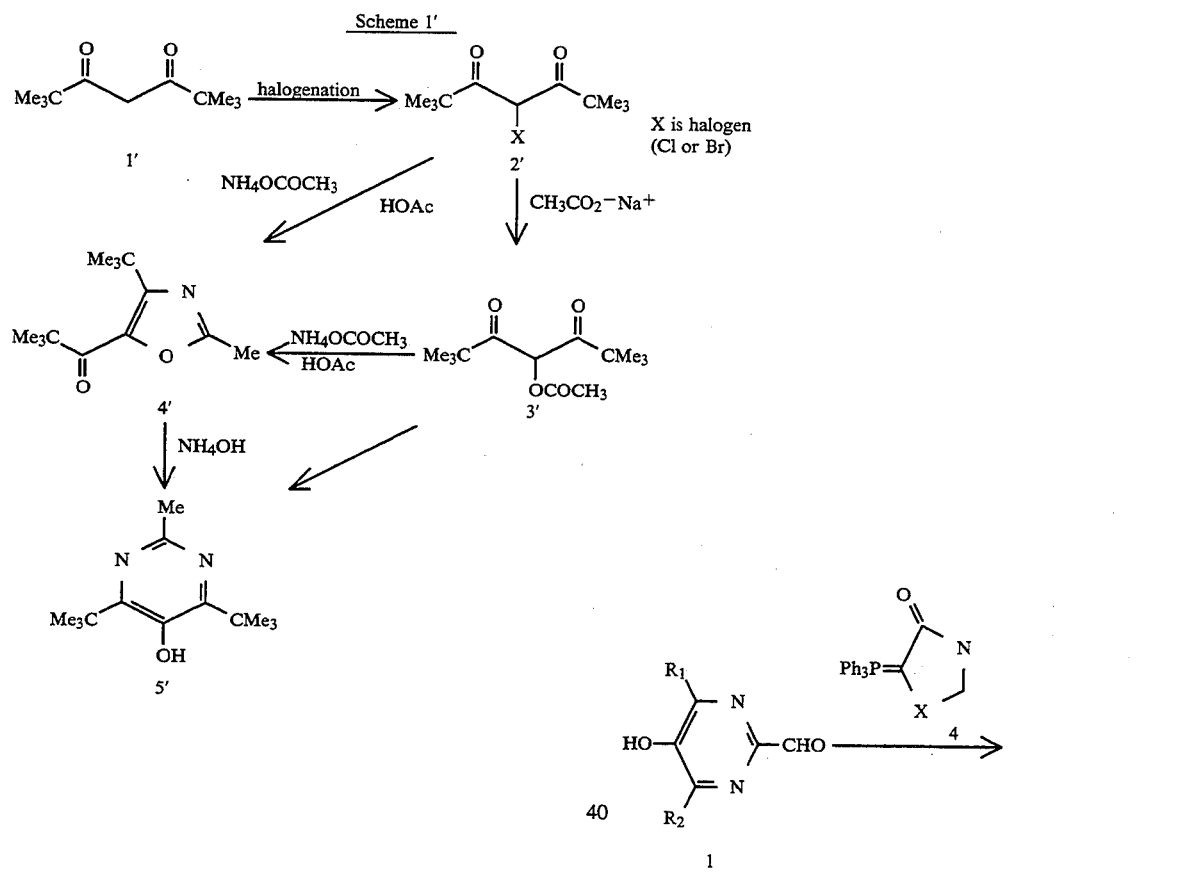

Compounds of the formula I may be prepared as shown in Schemes I–IV.

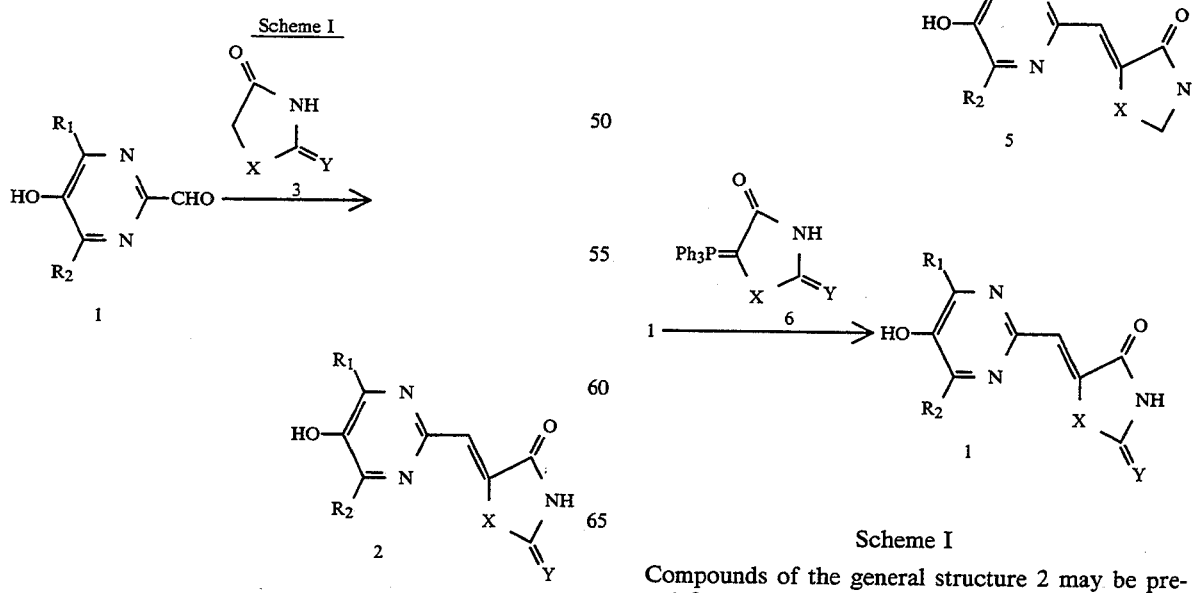

Scheme I

Compounds of the general structure 2 may be prepared from the aldehyde 1 by condensation with the heterocycle 3. The condensation may be done in a solvent such as acetic acid or toluene using a base such as sodium acetate or an amine base such as piperidine or β-alanine.

Scheme II

Compounds of the general structure 5 may be prepared from the aldehyde 1 by procedures analogous to those described in *Chem. Pharm. Bull. Japan* 34(4)16(9) (1986) and *J. Med. Chem.* 30, 1995 (1988). For example, reaction of 1 with 4 in a solvent such as toluene, dimethylformamide, tetrahydrofuran, or dimethylsulfoxide.

Alternatively, 4 may be prepared in situ from the corresponding phosphonium salt with a base such as t-butoxide or sodium hydride.

Compounds of the general structure 7 may alternatively be prepared by Witting reaction of 6 with 1.

Scheme III
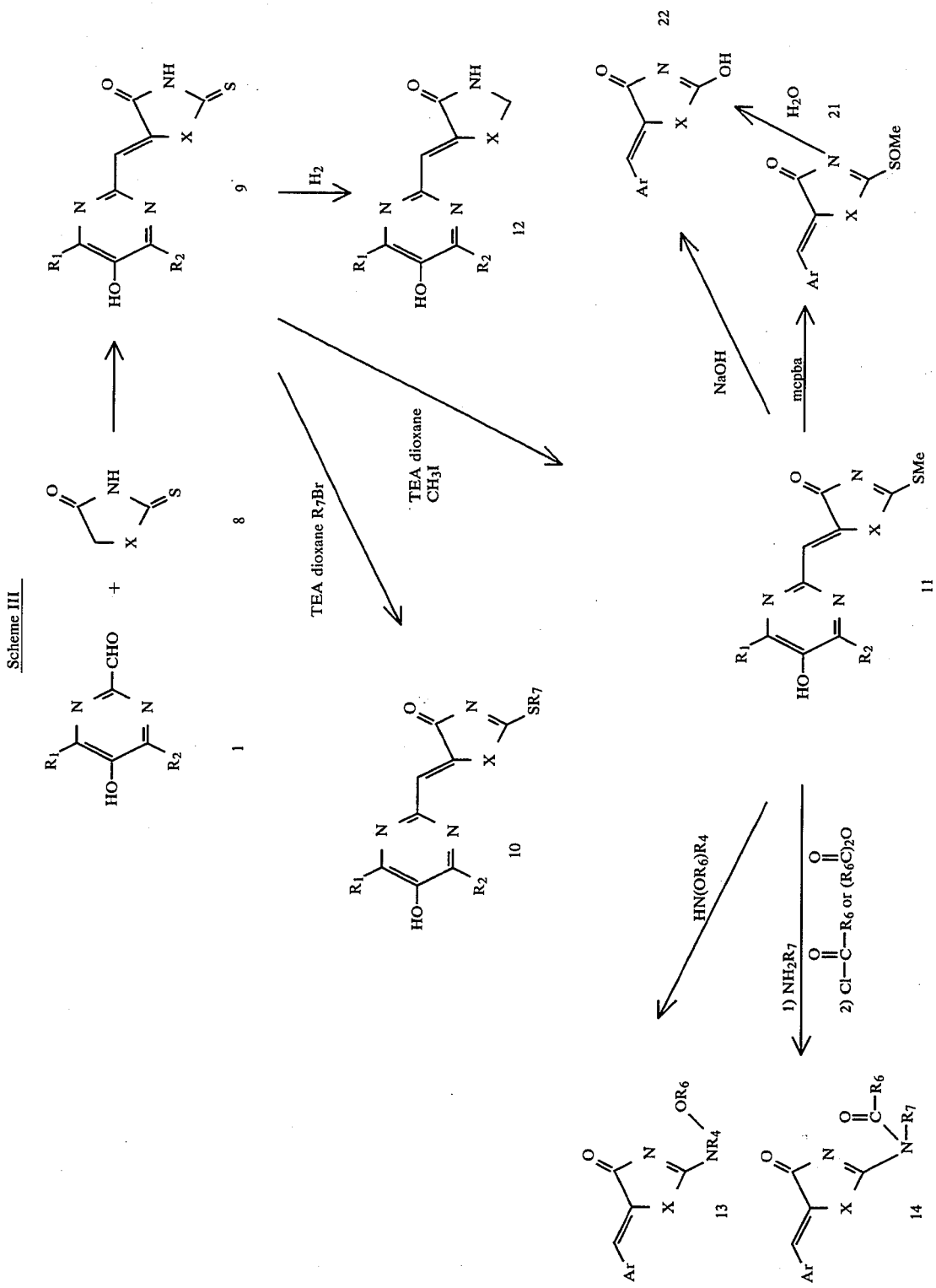

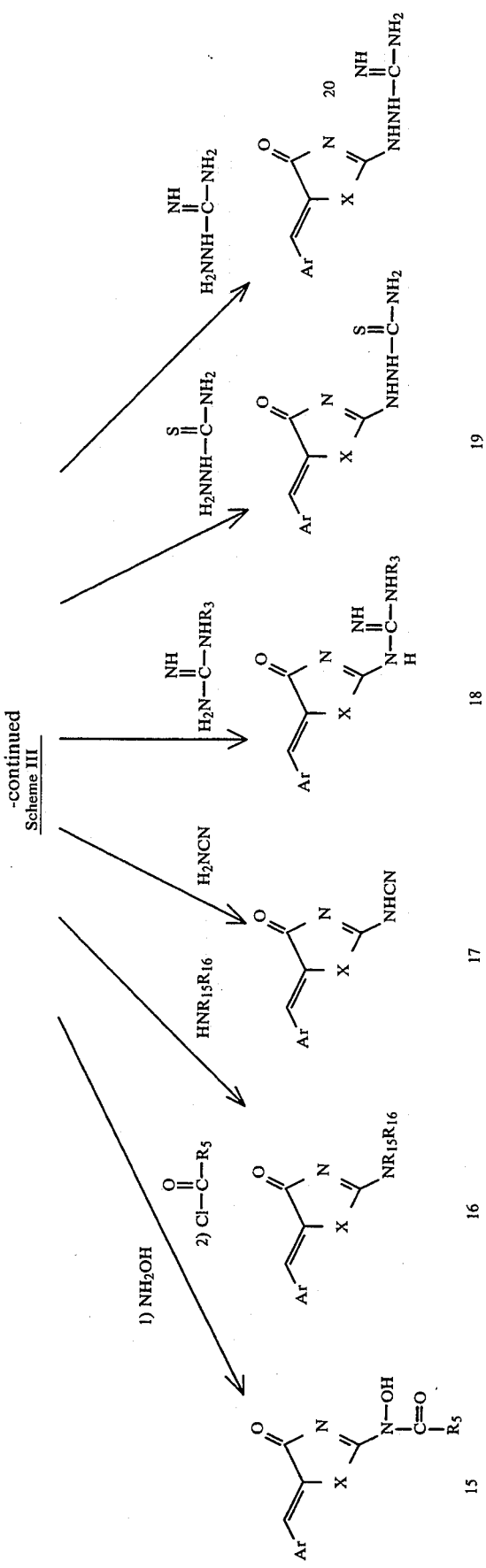

Scheme III hydrolysis of 11 to 22 with a reagent such as sodium hydroxide or potassium hydroxide.

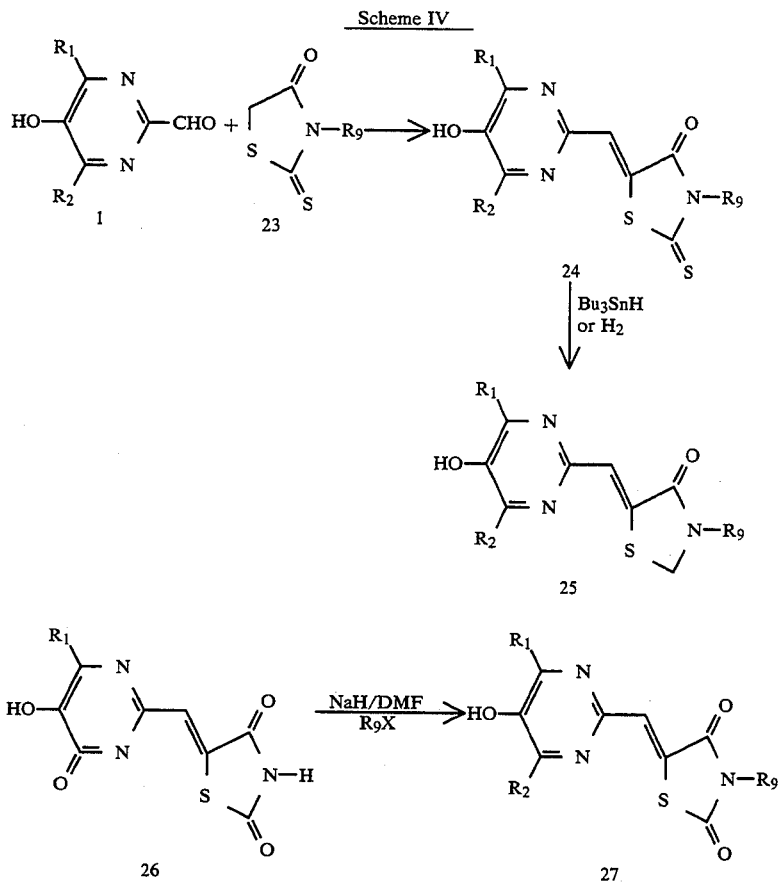

Compounds of formula 9 may be prepared from 1 by condensation with 8 by the procedures described in Scheme I. Reaction with R₇Br or methyl iodide in a solvent such as dioxane and using a base such as triethylamine gives 10 and 11 respectively.

Compounds of the formula 13–21 may be prepared by reaction of 11 with the appropriate nucleophile as shown in Scheme III in a solvent such as methanol, ethanol, or isopropanol at a temperature from room temperature to reflux.

Compounds of the formula 22 may be prepared by oxidation of 11 followed by hydrolysis or by direct R₉ is lower alkyl N-substituted compound 24 can be prepared by condensation of the aldehyde 1 with 23 using conditions analogous to those described in Scheme I for the N-unsubstituted compounds. The intermediates 23 are known or may be prepared by the procedures described in EPO 391 644A2. In certain cases compounds of the formula 27 may be prepared from the N-unsubstituted compounds 26 by alkylation with R₉X (X=Cl, Br) in the presence of a strong base such as NaH.

Schemes V and VI show the preparation of starting materials for each of Schemes I–IV beginning with the compound of the formula 5' from the preparation shown in Scheme 1'.

Scheme V

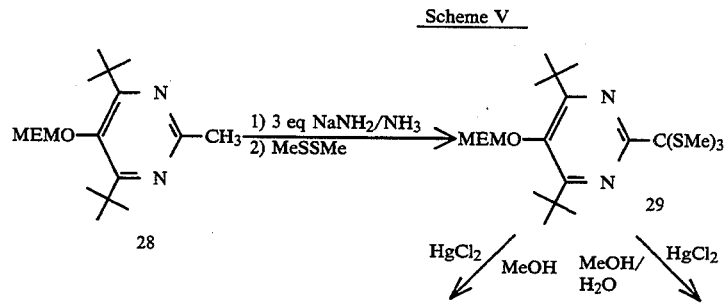

Scheme V

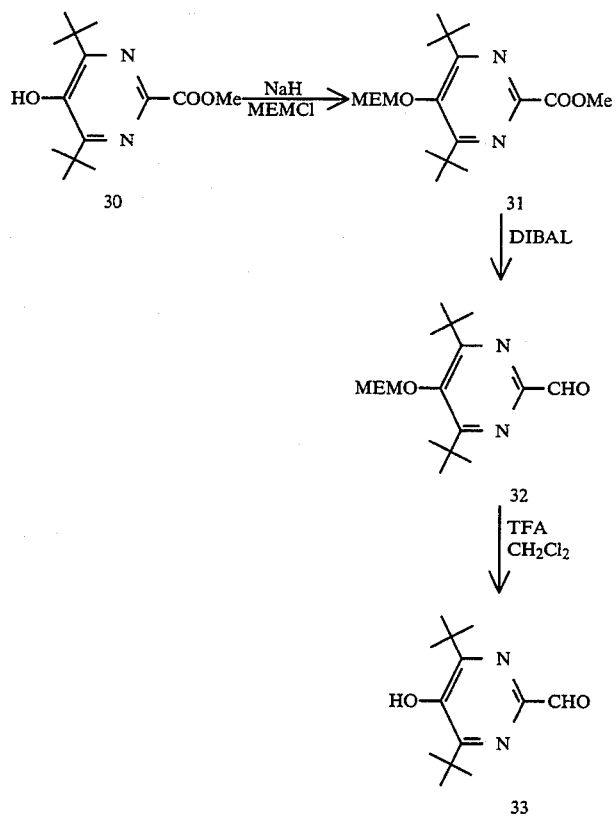

Starting aldehyde 1 (where $R_1=R_2=$t-bu) may be prepared from the 2-methyl compound 28 (ref: PD-4175 and PD-4176) by treatment with sodium amide in liquid ammonia, followed by treatment with dimethyldisulfide to give the intermediate orthoester 29. Treatment of 29 with mercuric chloride in anhydrous methanol gives the ester 30, which is converted to MEM derivative 31 by treatment with NaH and MEM-chloride. Compound 31 may be prepared directly from 29 by use of $HgCl_2$ in aqueous MeOH. DIBAL reduction of 31 gives aldehyde 32 which may be converted to 33 by dilute trifluoracetic acid in methylene chloride.

Scheme VI $R_1$ = H, Me, Et, Pr
$R_2$ = H, Me, Et, Pr

Starting aldehydes 34 (in which $R_1$ or $R_2$ is other than t-bu) may be prepared from the corresponding 2-SMe pyrimidines 35, by treatment with sodium cyanide, followed by reduction of the intermediate nitrile (36) with DIBAL. In certain cases it may by preferable to protect the 5-OH of nitrile 36 with a protecting group such as acetyl or MEM before the DIBAL reduction. SMe pyrimidines 35 may be prepared as described by Hurst (Heterocycles 22(1):9(1984) for $R_1=R_2=$Me.

One of skill in the art would recognize variations in the sequence and would recognize variations in the appropriate reaction conditions from the analogous reactions shown or otherwise known which may be appropriately used in the processes above to make the compounds of the formula I herein. For example, variations in the protecting groups are well known to an ordinary skilled artisan. Further, starting materials are known or can be prepared by known methods.

The products of the reactions described herein are isolated by conventional means such as extraction, distillation, chromatography, and the like.

The invention is further elaborated by the representative examples as follows. Such examples are not meant to be limiting.

EXAMPLE 1

4,6-Bis(1,1-dimethylethyl)-5-[(2-methoxyethoxy)methoxy]-2-pyrimidine carboxylic acid thiomethyl orthoester To a solution of sodium amide (602 mmol) in liquid ammonia is added 4,6-bis-(1,1-dimethylethyl)- 5-[(2-methoxyethoxy)-methoxy]-2-methylpyrimidine (53.4 g, 172.0 mmoles) dissolved in 50 mL of THF.

The reaction mixture is stirred for one half hour and then cooled to −78° C. Dimethyldisulfide (50.2 g, 533.2 mmoles) is added to the reaction mixture over 20 minutes. When addition is complete, the reaction mixture is warmed to reflux for 1 hour.

The reaction is quenched by the slow addition of 27 g of solid $NH_4Cl$ and the $NH_3$ is evaporated through a trap containing 500 mL of 10% (W/V) aqueous NaOH. The reaction mixture is partitioned between 200 mL of $Et_2O$ and 200 mL of 1.0 N NaOH. The aqueous layer is extracted with $Et_2O$ (3×200 mL). The combined organic extracts are washed with 1.0N NaOH (2×100 mL) and 100 mL of brine. Drying over $MgSO_4$ and evaporation of the solvent gives 80.5 g (100%) of the desired orthoester as an oil.

EXAMPLE 2

4,6-Bis-(1,1-dimethylethyl)-5-hydroxy-2-pyrimidine carboxylic acid methyl ester $HgCl_2$ (73.05 g, 269.1 mmoles) is added slowly to a solution of 4,6-bis-(1,1-dimethylethyl)-5-[(2-methoxyethoxy)methoxy]-2-pyrimidine carboxylic acid thiomethyl orthoester (80.5 g, 179.4 mmoles) in 400 mL of MeOH at room temperature and the reaction mixture is stirred for 1 additional hour.

The reaction mixture is diluted with 400 mL of $CH_2Cl_2$ and stirred for 10 minutes. The precipitate is removed by filtration through celite and the filtrate is concentrated on the rotovap. The residue is taken up in 300 mL of $CH_2Cl_2$ and washed with saturated $NH_4Cl$ (3×100 mL). Drying over $MgSO_4$ and evaporation of the solvent gives a brown solid.

Recrystallization from 200 mL of hexane gives 30.0 g (63%) of the desired ester. MP=131°–133° C.

EXAMPLE 3

4,6-Bis-(1,1-dimethylethyl)-5[(2-methoxyethoxy)methoxy]-2-pyrimidine carboxylic acid methyl ester 4,6-Bis-(1,1-dimethylethyl)-5-[(2-methoxyethoxy)methoxy]-2-pyrimidine carboxylic acid thiomethyl orthoester (41.8 g, 93.1 mmoles) is dissolved in 400 mL of 5% $H_2O$/MeOH, and cooled in a dry ice/acetone bath to −40° C. $H_2O$ (32.3 g, 149.0 mmoles) and $HgCl_2$ (101.2 g, 372.6 mmoles) are added to the reaction mixture, and the dry ice/acetone bath is removed. The solution is allowed to warm to room temperature for 1 hour. The reaction mixture is diluted with 500 mL of $CH_2Cl_2$ and stirred for 5 minutes. The solid is removed by filtration, and the filtrate is concentrated on the rotovap. The residue is taken up in 500 mL of $CH_2Cl_2$ and washed with saturated $NH_4Cl$ (2×200 mL) followed by 100 mL of brine. Drying over $MgSO_4$ and evaporation of solvent gives a yellow oil. Flash chromatography in $Et_2O$ gives 23.9 g (79%) of the desired methyl ester.

EXAMPLE 4

4,6-Bis-(1,1-dimethylethyl)-5[(2-methoxyethoxy)methoxy]-2-pyrimidine carboxylic acid methyl ester A solution of 4,6-bis-(1,1-dimethylethyl)-5-hydroxy-2-pyrimidine carboxylic acid methyl ester (4.0 g, 15.0 mmoles) in 50 mL of THF is added to a suspension of NaH (0.39 g, 16.5 mmoles) in THF (50 mL) at 0° C. When addition is complete, the reaction mixture is stirred at 0° C. for 15 minutes. 2-methoxyethoxymethyl chloride (2.0 g, 16.5 mmoles) is added and the solution is warmed to room temperature. The reaction mixture is stirred at room temperature overnight. It is diluted with 100 mL $H_2O$ and 100 mL of saturated aqueous $NH_4Cl$. The layers are separated, and the aqueous phase is washed with $Et_2O$ (3×100 mL). The combined organic phases are washed with 100 mL brine and dried over $MgSO_4$. Evaporation of $Et_2O$ gives 5.3 g (100%) of the desired ester as an oil.

EXAMPLE 5

4,6-Bis-(1,1-dimethylethyl)-5-[(2-methoxyethoxy)methyl]-2-pyrimidine carboxaldehyde A solution of di-isobutylaluminum hydride (22.6 mL, 1.5M in toluene) is added slowly (over a period of 30 minutes) to a solution of 4,6-bis-(1,1-dimethylethyl)-5-[(2-methoxyethoxy)methoxy]-2-pyrimidine carboxylic acid methyl ester (10.0 g, 28.2 mmoles) in 100 mL of toluene at −78° C. under an argon atmosphere.

After 3 hours, additional di-isobutyl aluminum hydride (6.2 mL, 1.5M, in toluene) is added to this reaction mixture at −78° C., and the mixture is stirred at −78° C. for an additional 2 hours. The reaction is quenched with 100 mL of 10% $HOAc/H_2O$, and the mixture is warmed to room temperature. The organics are extracted into $Et_2O$ (3×100 mL). The combined organic layers are washed with 100 mL of 10% $HOAc/H_2O$ followed by 100 mL of brine. Drying over $MgSO_4$ followed by evaporation of solvent gives 8.9 g (97%) of the desired aldehyde as an oil.

EXAMPLE 6

5-[[4,6-Bis-(1,1-dimethylethyl)-5-hydroxy-2-pyrimidinyl]methylene]-2-thioxo-4-thiazolidinone A mixture of 4,6-bis-(1,1-dimethylethyl)-5-[(2-methoxyethoxy)methoxy]-2-pyrimidine carboxaldehyde (0.5 g, 1.5 mmoles), rhodanine (0.25 g, 1.8 mmoles), and β-alanine (0.27 g, 3.1 mmoles) in acetic acid is heated at reflux for 1.5 hours. This solution is cooled to room temperature and diluted with 100 mL of water. The precipitate is collected by filtration and recrystallized from isopropyl ether/hexane. Yield of 5-[[4,6-bis-(1,1-dimethylethyl)-5-hydroxy-2-pyrimidinyl]methylene]-2-thioxo-4-thiazolidinone=0.26 g (48%). MP=257°–261° C. dec.

EXAMPLE 7

5-[[4,6-Bis-(1,1-dimethylethyl]-5-hydroxy-2-pyrimidinyl]methylene]-2-imino-4-thiazolidinone 4,6-Bis-(1,1-dimethylethyl)-5-[(2-methoxyethoxy)methoxy]-2-pyrimidine carboxaldehyde (0.5 g, 1.5 mmoles) is treated with β-alanine (0.27 g, 3.1 mmoles) and pseudothiohydantoin (0.21 g, 1.8 mmoles) according to the procedure of Example 6 to give 0.056 g (11%) of 5-[[4,6-bis-(1,1-dimethylethyl]-5-hydroxy-pyrimidinyl]-methylene]-2-imino-4-thiazolidinone. MP=278°–281° C. dec.

EXAMPLE 8

5-[[4,6-Bis-(1,1-dimethylethyl)-5-hydroxy-2-pyrimidinyl]methylene]-2,4-thiazolidinedione 4,6-Bis-(1,1-dimethylethyl)-5-[(2-methoxyethoxy)methoxy]-2-pyrimidine carboxaldehyde (0.5 g, 1.5 mmoles) is treated with β-alanine (0.27 g, 3.1 mmoles) and 2,4-thiazolidinedione (0.22 g, 1.8 mmoles) according to the procedure of Example 6 to give 0.12 g (25%) of 5-[[4,6-bis-(1,1-dimethylethyl]-5-hydroxy-2-pyrimidinyl]methylene]-2,4-thiazolidinedione. MP=229°–232° C. dec.

The following examples show the preparation of 4,6-bis(1,1-dimethylethyl)-5-[(2-methoxyethoxy)methoxy]-2-methylpyrimidine for use in Example 1 (see copending application U.S. application Ser. No. 07/648,115, filed Jan. 31, 1991).

EXAMPLE 9

1-[4(1,1-Dimethylethyl)-2-methyl-5-oxazolyl]2,2-dimethyl-1-propanone

A solution of 4-(acetyloxy)-2,2,6,6-tetramethyl 3,5-heptanedione (22 g, 0.09 mol) in acetic acid (100 mL) is treated with ammonium acetate (44 g). The reaction mixture is heated at reflux overnight. The reaction mixture is diluted with water and neutralized (to pH 5) by the addition of aqueous sodium hydroxide. The product is extracted into ethyl acetate (3×150 mL) and the combined organic layers are washed with 0.1N NaOH, water, and then brine. The organic layer is dried and evaporated. The residue is taken up in hexane (50 mL) and applied to a pad of silica gel (500 g). The silica pad is eluted with hexane (100 mL). Then the product is eluted from the silica with hexane/ethyl acetate (4:1) to give 18.6 g (91%) of 1-[4-(1,1-dimethylethyl)-2-methyl-5-oxazolyl]-2,2-dimethyl-1-propanone as an oil.

$^1$H NMR (CDCl$_3$) δ 2.60 (s, 3H, 2-Me), 1.35 (s, 9H, tbu), 1.31 (s, 9H, tbu). $^{13}$C-NMR (CDCl$_3$) δ 195.8, 159.3, 157.6, 143.6, 44.2, 32.7, 28.4, 26.6.

EXAMPLE 10

4,6-Bis(1,1-dimethylethyl)-5-hydroxy-2-methylpyrimidine

A mixture of 1-[4-(1,1-dimethylethyl-2-methyl-5-oxazolyl]-2,2-dimethyl-1-propanone (8.5 g, 38 mmol) and concentrated ammonium hydroxide (100 mL) is heated at 180° C. for 36 hours in a steel bomb. The reaction mixture is cooled and the excess ammonia is evaporated on the rotovap. The pH of the resulting mixture is adjusted to pH 6 with concentrated HCl with ice bath cooling. The product is extracted into ether (3×25 mL) and the organic layer is dried (MgSO$_4$) and evaporated. The residue is purified by flash chromatography (silica, 7% EtOAc/hexane) to give pure 4,6-bis(1,1-dimethylethyl)-5-hydroxy-2-methylpyrimidine (6.35 g, 75%) as a partial hydrate; mp 62°–65° C.

$^1$H-NMR (d$_6$-DMSO) δ 7.76 (br, 1H, OH), 2.45 (s, 3H, CH$_3$), 1.36 (s, 18H, t-bu).

$^{13}$C-NMR (CDCl$_3$) δ 161.2, 157.5, 145.1, 37.0, 28.7, 25.4.

The compound is further characterized by conversion to its acetyl derivative, mp 45°–47° C.

EXAMPLE 11

4,6-Bis(1,1-dimethylethyl)-5-[(2-methoxyethoxy)methoxy]-2-methylpyrimidine 4,6-Bis(1,1-dimethylethyl)-5-hydroxy-2-methyl pyrimidine (9.8 g, 44.1 mmoles) is dissolved in 100 mL of tetrahydrofuran and added dropwise to a suspension of sodium hydride (1.2 g, 48.5 mmoles) in THF (50 mL) at 0° C. The reaction mixture is warmed to room temperature over 15 minutes. 2-Methoxyethoxymethyl chloride (7.1 g, 57.3 mmoles) is added to the reaction mixture at room temperature. After being stirred at room temperature for 4 hours, the reaction is quenched by the addition of saturated ammonium chloride and the tetrahydrofuran is evaporated. The organics are extracted into 300 mL of ether. The ether is washed with 100 mL of brine and dried over magnesium sulfate. Evaporation of the solvent gives the crude product which is purified by flash chromatography (silica, 10% ether/hexane). Yield of 4,6-bis(1,1-dimethylethyl)-5-[(2-methoxyethoxy)methoxy]-2-methylpyrimidine=11.3 g (82%) as a clear oil.

$^1$H-NMR (CDCl$_3$) δ 4.96 (s, 2H, O—CH$_2$—O), 3.93 (m, 2H), 3.60 (m, 2H), 3.39 (s, 3H, O—CH$_3$), 2.54 (s, 3H, CH$_3$), 1.40 (s, 18H, C(CH$_3$)$_3$).

C$^{13}$-NMR (CDCl$_3$) δ 169.2, 159.8, 145.7, 99.9, 71.5, 69.4, 58.9, 38.2, 30.0, 25.2.

EXAMPLE 12

5-[[4,6-Bis(1,1-dimethylethyl)-5-hydroxy-2-pyrimidinyl]methylene]-3-amino-2-thioxo-4-thiazolidinone A mixture of 4,6-bis(1,1-dimethylethyl)-5-hydroxy-2-pyrimidine carboxaldehyde (1.00 g, 4.23 mmol), sodium acetate (1.36 g, 16.6 mmol), and 3-aminorhodanine (0.63 g, 4.3 mmol) in glacial acetic acid (15 mL), under nitrogen atmosphere, is warmed to reflux and refluxed 7 hours. This mixture is then cooled to room temperature and stirred 16 hours. After stirring, the reaction mixture is diluted with a 1:2 mixture of ethanol and water and extracted with ethyl acetate. The combined organic extracts are washed with water, aqueous 0.2N hydrochloric acid solution, and brine. The organic phase is dried over magnesium sulfate, concentrated, and purified by flash chromatography (SiO$_2$, 20% ethyl acetate/hexane) followed by recrystallization from methanol and water to give 0.42 g (27%) of the title compound, mp 194°–196° C.

EXAMPLE 13

5-[[4,6-Bis(1,1-dimethylethyl)-5-hydroxy-2-pyrimidinyl]methylene]-3-methyl-2-thioxo-4-thiazolidinone A mixture of 4,6-bis(1,1-dimethylethyl)-5-hydroxy-2-pyrimidine carboxaldehyde (0.50 g, 2.1 mmol), sodium acetate (0.60 g, 7.3 mmol), and 3-methylrhodanine (0.31 g, 2.1 mmol) in glacial acetic acid (10 mL) is placed under nitrogen atmosphere and warmed to reflux. After refluxing 21 hours, the mixture is cooled to room temperature and diluted with a 1:1 mixture of ethanol and water. The resulting slurry is stirred 0.5 hours and filtered. The precipitate is recrystallized from methanol and water to give 0.36 g (47%) of the title compound, mp 226°–228° C.

EXAMPLE 14

5-[[4,6-Bis(1,1-dimethylethyl)-5-hydroxy-2-pyrimidinyl]methylene]-3-(dimethylamino)-2-thioxo-4-thiazolidinone A mixture of 4,6-bis(1,1-dimethylethyl)-5-hydroxy-2-pyrimidine carboxaldehyde (0.30 g, 1.3 mmol), sodium acetate (0.42 g, 5.1 mmol), and [[(2,2-dimethylhydrazino)thioxmethyl]thio]acetic acid (0.37 g, 1.3 mmol) (See Hanefeld, W., Jalili, M. A., Arch. Pharm. 1987, 320, 329) in glacial acetic acid (10 mL) is placed under nitrogen atmosphere and warmed to reflux. After refluxing 20 hours, this mixture is cooled to room temperature, diluted with a 1:2 mixture of ethanol and water, and extracted with ethyl acetate. The combined extracts are washed with water and brine, dried over magnesium sulfate, and concentrated under vacuum. The residue is purified by flash chromatography (SiO$_2$, 20% ethyl acetate/hexane), followed by recrystallization in methanol and water to give 0.22 g (44%) of the title compound, mp 100°–105° C. (decomposes).

EXAMPLE 15

3-[[4,6-Bis-(1,1-dimethylethyl)-5-hydroxy-2-pyrimidinyl]methylene]-N-methoxy-pyrrolidin-2-one Triphenylphosphine (1.5 g, 5.7 mmol) is added to a solution of N-methoxy-3-bromopyrrolidin-2-one (Ikuta, et al. J. Med. Chem. 1984, 30, 1995) (1.0 g, 5.2 mmol) in THF (10 mL) and the mixture is warmed to reflux under an argon atmosphere for 12 hours. The reaction mixture is cooled in an ice bath and the solvent is decanted away from the resulting solid. The solid is added to a solution of triethylamine (0.93 g, 9.3 mmol) and 4,6-bis-(1,1-dimethylethyl)-5-hydroxypyrimidine-2-carboxaldehyde (0.97 g, 4.1 mmol) in ethanol (10 mL). The resulting mixture is warmed to reflux for 3 hours under an argon atmosphere. The mixture is cooled to room temperature, the EtOH is evaporated and the residue is partitioned between 50 mL EtOAc and 50 mL H₂O. The organic extract is dried over MgSO₄. The solvent is evaporated and the solid is recrystallized from Et₂O/hexane. Yield of 3-[[4,6-bis-(1,1-dimethylethyl)-5-hydroxy-2-pyrimidinyl]methylene]-N-methoxypyrrolidin-2-one=0.34 g (20%), mp 184°–186° C.

EXAMPLE 16

α-[[4,6-Bis(1,1-dimethylethyl)-5-hydroxy-2-pyrimidinyl]methylene]-γ-butyrolactone A solution of 4,6-bis(1,1-dimethylethyl)-5-hydroxypyrimidine-2-carboxaldehyde (0.5 g, 2.1 mmol) and α-triphenylphosphoranylidene-γ-butyrolactone (Katsumi, et al. Chem. Pharm. Bull. [Japan]1986, 34, 619) (0.95 g, 2.8 mmol) in 50 mL of toluene is warmed to 60° C. overnight. The toluene is evaporated and the residue purified by flash chromatography (silica, 20% EtOAc/hexane). Recrystallization from hexane gives 0.4 g (62%) of α-[[4,6-bis(1,1-dimethylethyl)-5-hydroxy-2-pyrimidinyl]methylene]-γ-butyrolactone, mp 158°–160° C.

EXAMPLE 17

5-[[4,6-Bis(1,1-dimethylethyl)-5-hydroxy-2-pyrimidinyl]methylene]-2-(methylthio)-4(5H)-thiazolone To a solution of 5-[[4,6-bis(1,1-dimethylethyl)-5-hydroxy-2-pyrimidinyl]methylene]-2-thioxo-4-thiazolidinone (1.00 g, 2.85 mmol) and diisopropylethylamine (0.75 g, 5.8 mmol) in tetrahydrofuran (20 mL) under nitrogen atmosphere is added methyl iodide (0.80 g, 5.6 mmol). The resulting mixture is stirred 16 hours, diluted with ethyl acetate, and with aqueous 1N hydrochloric acid solution and brine. The organic phase is dried over magnesium sulfate, concentrated, and purified by flash chromatography (SiO₂, 10% ethyl acetate/hexane) followed by recrystallization from ethyl acetate and hexane to give 0.62 g (60%) of the title compound, mp 205°–208° C.

We claim:
1. A method of treating inflammation in a human in need of such treatment which comprises administering a compound of the formula

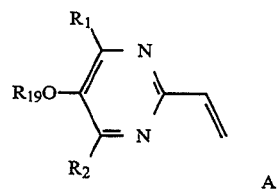

or a pharmaceutically acceptable acid addition or base salt thereof; wherein
R₁ and R₂ are tertiarybutyl;
R₁₉ is H;
A is
1)

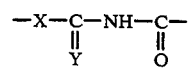

wherein
X is S, O, NH, or CH₂; and
Y is S, O, or NH;
2)

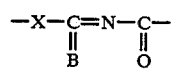

wherein
X is as defined above; and
B is
  i) SR₇,
  ii) SOR₇,
  iii) SO₂R₇,
  iv) NR₁₅R₁₆,
  v) NHCN,
  vi)

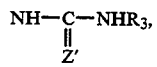

vii)

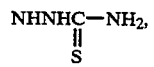

viii)

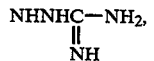

ix) N(OR₆)R₄,
  x) N(OH)COR₅,
  xi) NR₄W,
  xii) S(CH₂)ₙCO₂R₆, or
  xiii) NR₇COR₆
  wherein
  Z' is S, O, NH, or NCN;
  W is CO₂R₇,

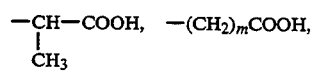

-continued
—(CH$_2$)$_m$OH or C(CH$_2$OH)$_3$;

n is 1, 2, or 3;
m is 1, 2, 3, 4, or 5;
R$_{15}$ and R$_{16}$ are independently H, lower alkyl, aralkyl, or (CH$_2$)$_n$NR$_6$R$_7$ wherein n is as defined above;
R$_3$ is H, alkyl, or aryl;
R$_4$ is H or alkyl;
R$_5$ is alkyl, aryl, or CF$_3$;
R$_6$ is H or lower alkyl; and
R$_7$ is lower alkyl;

3)

$$-CH_2CH_2-Z-\overset{\overset{O}{\|}}{C}-$$

wherein Z is CH$_2$, S, O, or NR$_8$
wherein R$_8$ is H, lower alkyl, OH, or OMe; or

4)

$$-S(O)_p-\underset{\underset{R_9}{|}}{\overset{\overset{W_1}{\|}}{C}}-N-\overset{\overset{O}{\|}}{C}-$$

wherein
p is 0, 1, or 2;
W$_1$ is H$_2$, O, or S;
R$_9$ is
 i) lower alkyl,
 ii) lower alkenyl,
 iii) SO$_2$CH$_3$,
 iv) OR$_{10}$,
 v)

$$-\overset{\overset{O}{\|}}{C}R_{11},$$

vi) NR$_{12}$R$_{13}$, or
 vii) -(CH$_2$)$_n$Y$_1$
  wherein
  n is as defined above;
R$_{10}$ is H, lower alkyl, tosyl, or $$-\overset{\overset{O}{\|}}{C}-R_7;$$

Y$_1$ is —CN, —OR$_{10}$, SH, SR$_7$, $$-\overset{\overset{O}{\|}}{C}-R_{14}, \quad NR_{12}R_{13}$$

NR$_{12}$R$_{13}$ wherein R$_{12}$ and R$_{13}$ are as defined herein,
wherein
R$_7$ and R$_{10}$ are as defined above;
R$_{11}$ is lower alkyl, lower alkoxy, or NH$_2$
R$_{14}$ is -OH, lower alkyl, lower alkoxy, or NH$_2$
R$_{12}$ and R$_{13}$ are each independently H, lower alkyl, lower alkenyl, (CH$_2$)$_q$OH, (CH$_2$)$_q$NR$_{17}$R$_{18}$, or (CH$_2$)$_q$SR$_7$, or R$_{12}$ and R$_{13}$ taken together form a morpholinyl, piperidinyl, piperazinyl, or an N-methyl piperazinyl ring,
wherein
R$_7$ is as defined above;
q is an integer of 1-6;
R$_{17}$ and R$_{18}$ are independently lower alkyl, in unit dosage form.

2. A method of treating GI ulcers in a human in need of such treatment which comprises administering a compound of the formula $$\underset{R_2}{\overset{R_1}{\diagup}}\!\!\diagdown\!\! \text{pyrimidine with } R_{19}O\text{, vinyl, A substituent} \quad I$$

or a pharmaceutically acceptable acid addition or base salt thereof;
wherein
R$_1$ and R$_2$ are tertiarybutyl;
R$_{19}$ is H;
A is

1)

$$-X-\underset{\underset{Y}{\|}}{C}-NH-\overset{\overset{O}{\|}}{C}-$$

wherein
X is S, O, NH, or CH$_2$; and
Y is S, O, or NH;

2)

$$-X-\underset{\underset{B}{\|}}{C}=N-\overset{\overset{O}{\|}}{C}-$$

wherein
X is as defined above; and
B is
 i) SR$_7$,
 ii) SOR$_7$,
 iii) SO$_2$R$_7$,
 iv) NR$_{15}$R$_{16}$,
 v) NHCN,
 vi)

$$NH-\underset{\underset{Z'}{\|}}{C}-NHR_3,$$

vii)

$$NHNH\overset{\overset{S}{\|}}{C}-NH_2,$$

viii)

$$NHNH\overset{\overset{NH}{\|}}{C}-NH_2,$$

ix) N(OR$_6$)R$_4$,
 x) N(OH)COR$_5$, xi) NR$_4$W,
xii) S(CH$_2$)$_n$CO$_2$R$_6$, or
xiii) NR$_7$COR$_6$
   wherein
   Z' is S, O, NH, or NCN;
   W is CO$_2$R$_7$,

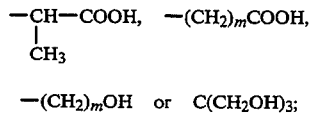

—(CH$_2$)$_m$OH or C(CH$_2$OH)$_3$;

n is 1, 2, or 3;
m is 1, 2, 3, 4, or 5;
R$_{15}$ and R$_{16}$ are independently H, lower alkyl, aralkyl, or (CH$_2$)$_n$NR$_6$R$_7$
   wherein n is as defined above;
R$_3$ is H, alkyl, or aryl;
R$_4$ is H or alkyl;
R$_5$ is alkyl, aryl, or CF$_3$;
R$_6$ is H or lower alkyl; and
R$_7$ is lower alkyl;

3)

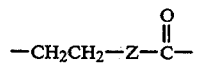

wherein Z is CH$_2$, S, O, or NR$_8$
wherein R$_8$ is H, lower alkyl, OH, or OMe; or

4)

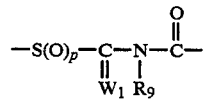

wherein
p is 0, 1, or 2;
W$_1$ is H$_2$, O, or S;
R$_9$ is
   i) lower alkyl,
   ii) lower alkenyl,
   iii) SO$_2$CH$_3$,
   iv) OR$_{10}$,
   v)

vi) NR$_{12}$R$_{13}$, or
   vii) -(CH$_2$)$_n$Y$_1$
wherein
n is as defined above;
R$_{10}$ is H, lower alkyl, tosyl, or

Y$_1$ is —CN, —OR$_{10}$, SH, SR$_7$,

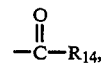

NR$_{12}$R$_{13}$ wherein R$_{12}$ and R$_{13}$ are as defined herein,
wherein
R$_7$ and R$_{10}$ are as defined above;
R$_{11}$ is lower alkyl, lower alkoxy, or NH$_2$
R$_{14}$ is —OH, lower alkyl, lower alkoxy, or NH$_2$
R$_{12}$ and R$_{13}$ are each independently H, lower alkyl, lower alkenyl, (CH$_2$)$_q$OH, (CH$_2$)$_q$NR$_{17}$R$_{18}$, or (CH$_2$)$_q$SR$_7$, or R$_{12}$ and R$_{13}$ taken together form a morpholinyl, piperidinyl, piperazinyl, or an N-methyl piperazinyl ring,
wherein
R$_7$ is as defined above;
q is an integer of 1–6;
R$_{17}$ and R$_{18}$ are independently lower alkyl, in unit dosage form.

* * * * *

UNITED STATES PATENT AND TRADEMARK OFFICE
CERTIFICATE OF CORRECTION

PATENT NO. : 5,348,957

DATED : September 20, 1994

INVENTOR(S) : Belliotti et al

It is certified that error appears in the above-indentified patent and that said Letters Patent is hereby corrected as shown below:

Column 3, lines 25-34, replace

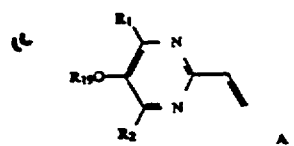

with

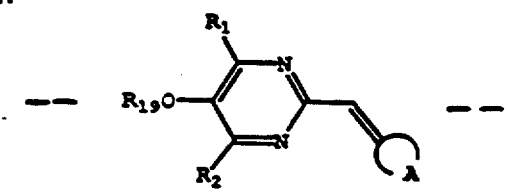

Column 30, lines 1-9, replace

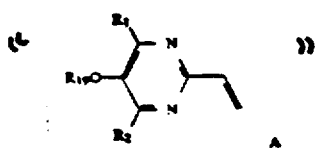

with

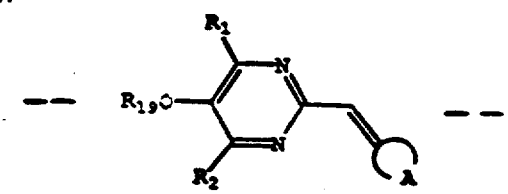

UNITED STATES PATENT AND TRADEMARK OFFICE
CERTIFICATE OF CORRECTION

PATENT NO. : 5,348,957

DATED : September 20, 1994

INVENTOR(S) : Belliotti et al

It is certified that error appears in the above-indentified patent and that said Letters Patent is hereby corrected as shown below:

Column 31, line 59, delete "$NR_{12}R_{13}$".

Column 32, lines 11-19, replace       with

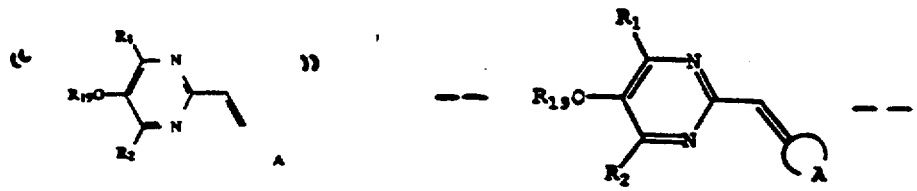

Signed and Sealed this

Twelfth Day of September, 1995

Attest:

BRUCE LEHMAN

Attesting Officer

Commissioner of Patents and Trademarks